United States Patent [19]

Whitehead et al.

[11] Patent Number: 5,196,534
[45] Date of Patent: Mar. 23, 1993

[54] PROCESS FOR THE PREPARATION OF LACTAM DERIVATIVES

[75] Inventors: John W. F. Whitehead; Keith Mills, both of Ware; Ian H. Coates, Hertford; Alexander W. Oxford; Peter C. North, both of Royston, all of England

[73] Assignee: Glaxo Group Limited, London, England

[21] Appl. No.: 704,099

[22] Filed: May 22, 1991

[30] Foreign Application Priority Data

May 23, 1990 [GB] United Kingdom ............... 9011469

[51] Int. Cl.$^5$ ............................................. C07D 471/04
[52] U.S. Cl. ......................................... 546/86; 546/87; 546/220
[58] Field of Search ............................ 546/86, 87

[56] References Cited

U.S. PATENT DOCUMENTS 3,316,271 4/1967 Cohen et al. ...................... 546/86
4,985,422 1/1991 North et al. ....................... 514/215

FOREIGN PATENT DOCUMENTS 0306323 3/1989 European Pat. Off. ........... 546/86
0353983 2/1990 European Pat. Off. ........... 546/86

OTHER PUBLICATIONS

Mar., Advanced Organic Chemistry, Second Edition, p. 326 McGraw-Hill pub. 1979.

*Primary Examiner*—Alan L. Rotman
*Attorney, Agent, or Firm*—Bacon & Thomas

[57] ABSTRACT

The invention relates to a process for the preparation of a compound of formula (I)

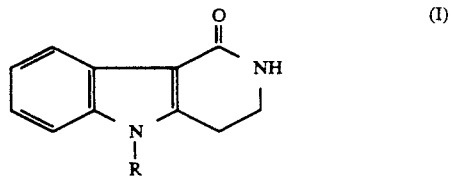

wherein R represent a hydrogen atom or a methyl or ethyl group, which comprises cyclising a compound of formul (IV)

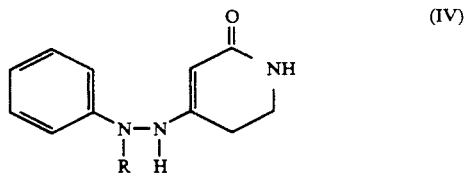

Where R represents a hydrogen atom, the compound of formula (IV) may optionally be alkylated to produce a compound in whcich R is methyl or ethyl.

The compound of formula (I) is useful as an intermediate in the preparation of 2,3,4,5-tetrahydro-2-[(imidazol-4(or 5)-yl)methyl]-1H-pyrido[4,3-b]indol-1-ones having 5-HT$_3$ antagonist activity.

9 Claims, No Drawings

PROCESS FOR THE PREPARATION OF LACTAM DERIVATIVES

This invention relates to a process for the preparation of compounds which are useful as intermediates in the preparation of pharmaceutical compounds.

The compounds of formula (I):

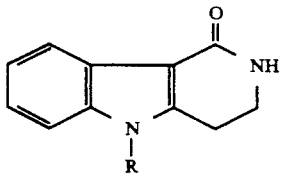

(I)

wherein R represents a hydrogen atom or a methyl group, are useful intermediates in the preparation of 2,3,4,5-tetrahydro-2-[(imidazol-4 (or 5)-yl)methyl]-1H-pyrido[4,3-b]indol-1-ones, such as those disclosed in EP-A-306323. In particular the compound of formula (I) wherein R is a methyl group is useful in the preparation of 2,3,4,5-tetrahydro-5-methyl-2-[(5-methyl-1H-imidazol-4-yl)methyl]-1H-pyrido-[4,3-b]indol-1-one, and its physiologically acceptable salts and solvates.

The method for the preparation of the compounds of formula (I) described in EP-A-306323 involves a Beckmann rearrangement of an oxime of formula (II):

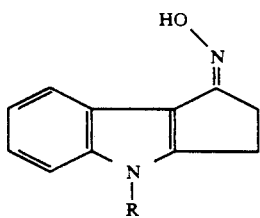

(II)

the oxime of formula (II) being prepared by the reaction of a ketone of formula (III):

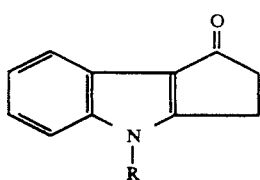

(III)

with hydroxylamine hydrochloride. The compounds of formula (III) are prepared according to the method of H. Iida et al., in *J. Org. Chem.* 1980, 45, 2938, i.e. by palladium (II) acetate catalysed cyclisation of the product obtained by the reaction of an aniline with 1,3-cyclopentanedione, followed by an optional N-methylation reaction.

An advantageous method for the preparation of compounds of formula (I) has now been discovered, which involves fewer reaction stages and gives the desired product in a higher overall yield.

Thus the present invention provides a process for the preparation of a compound of formula (I):

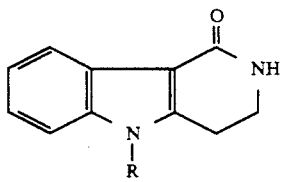

(I)

wherein R represents a hydrogen atom or a methyl or ethyl group, which comprises cyclising a compound of formula (IV):

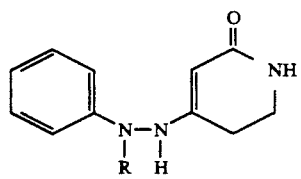

(IV)

wherein R is as defined previously, and when the compound of formula (I) wherein R represents a hydrogen atom is obtained, optionally alkylating this compound to give the compound of formula (I) wherein R represents a methyl or an ethyl group.

The reaction may be effected in the presence or absence of an acid catalyst.

When the reaction is effected in the presence of an acid catalyst, suitable acids include 80–100% w/w sulphuric acid, a mixture of 100% w/w sulphuric acid and glacial acetic acid, 85% orthophosphoric acid, and hydrocarbylsulphonic acids (e.g. methanesulphonic acid). When sulphuric acid is used, the reaction may be effected in the presence of a suitable co-solvent such as an alcohol (e.g. ethanol) or a halogenated hydrocarbon (e.g. dichloromethane).

The acid-catalysed reaction may conveniently be effected at a temperature in the range 0° to 100° C.

Alternatively, the reaction may be effected in the presence of a Lewis acid such as zinc chloride in acetic acid at an elevated temperature (e.g. 110° C.); or in the presence of polyphosphate ester in a halogenated hydrocarbon such as chloroform at the reflux temperature of the solvent.

In a yet further embodiment, the reaction may be carried out in the absence of catalyst at elevated temperature using a high boiling solvent, for example diethylene glycol at 180°.

Most preferably, the reaction is effected in the presence of 80–100% w/w sulphuric acid or a mixture of 100% w/w sulphuric acid and glacial acetic acid at a temperature in the range 0° to 30° C., most preferably 0° to 5° C.

The reaction of the compounds of formula (I) wherein R represents a hydrogen atom to give the compound of formula (I) wherein R represents a methyl or ethyl group may be effected with an alkylating agent (e.g. dimethylsulphate), in an organic solvent such as acetone, in the presence of a base such as dilute aqueous sodium hydroxide at an elevated temperature (e.g. 50° C.).

A preferred embodiment of the process of the invention comprises the cyclisation of the compound of formula (IV) wherein R represents a methyl group to give 2,3,4,5-tetrahydro-5-methyl-1H-pyrido[4,3-b]indol-1-one, i.e. the compound of formula (I) wherein R represents a methyl group.

A further preferred embodiment of the process according to the invention comprises the cyclisation of the compound of formula (IV) wherein R represents a hydrogen atom to give 2,3,4,5-tetrahydro-1H-pyrido[4,3-b]indol-1-one which is then methylated with a suitable methylating agent such as dimethyl sulphate to give 2,3,4,5-tetrahydro-5-methyl-1H-pyridol[4,3-b]indol-1-one.

Compounds of formula (IV) may be prepared, for example, by the reaction of a phenylhydrazine of formula PhNRNH$_2$ (i.e. phenylhydrazine, 1-methyl-1-phenylhydrazine or 1-ethyl-1-phenylhydrazine) with 2,4-piperidinedione. The reaction may conveniently be effected in a solvent such as an alcohol (e.g. ethanol), and at a temperature in the range 20°–25° C.

The phenylhydrazine used in the above reaction may be in the form of the free base, or a salt of the phenylhydrazine (e.g. a sulphate) may be used and the free base generated in situ.

2,4-Piperidinedione may also conveniently be prepared in situ, from a compound of formula (V):

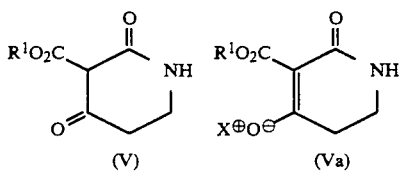

wherein R$^1$ represents a lower alkyl (e.g. methyl or ethyl) group, or an alkali metal (e.g. sodium) alkoxide thereof (i.e. a compound of formula (Va) wherein X$^+$ represents an alkali metal ion), by hydrolysis and decarboxylation under acidic conditions (e.g. at pH2), at an elevated temperature. Where necessary, the appropriate pH may be achieved by addition of a mineral acid (e.g. hydrochloric acid).

Compounds of formula (IV) may also be prepared directly from a compound of formula (V) or an alkali metal alkoxide thereof without isolation of 2,4-piperidinedione. Thus compounds of formula (IV) may be prepared by treating a compound of formula (V) or (Va) under acidic conditions (which may be achieved where necessary by addition of a mineral acid e.g. dilute hydrochloric acid) at an elevated temperature, followed by reaction of the resultant cooled solution with an appropriate phenylhydrazine, or a salt thereof, in the presence of an aqueous alkali metal hydroxide (e.g. aqueous sodium hydroxide).

Compounds of formula (V) and (Va) may be prepared from a compound of formula (VI):

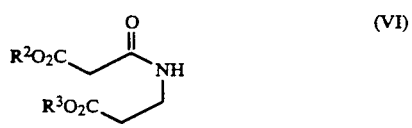

wherein R$^2$ and R$^3$ independently represent a lower alkyl (e.g. methyl or ethyl) group, by reaction with an alkali metal alkoxide (e.g. sodium methoxide) in an alcohol (e.g. methanol) at the reflux temperature of the solvent.

Compounds of formula (VI) are either known, or may be prepared by reaction of an alkyl ester of 3-aminopropionic acid with a malonic alkyl ester.

Thus an alkyl ester of 3-aminopropionic acid may be reacted directly with a malonic acid diester; or with a more reactive derivative of malonic acid, such as an acid chloride or a mixed acid anhydride; or with a malonic acid monoalkyl ester in combination with a suitable activating agent such as dicyclohexylcarbodiimide.

According to a further aspect, the invention provides a process for the preparation of compounds, particularly 5-HT$_3$ antagonists, containing the group

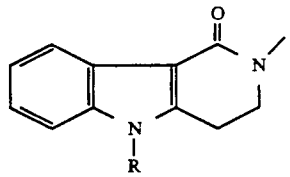

wherein R is as defined previously, which comprises reacting a compound of formula (I) prepared as described above, with an appropriate imidazole derivative (e.g. 4-hydroxymethyl-5-methylimidazole). Thus in accordance with this aspect of the invention, 2,3,4,5-tetrahydro-5-methyl-2-[(5-methyl-1H-imidazol-4-yl)methyl]-1H-pyrido[4,3-b]indol-1-one may be prepared from 2,3,4,5-tetrahydro-5-methyl-1H-pyrido[4,3-b]indol-1-one by reaction with 4-hydroxymethyl-5-methylimidazole or a salt (e.g. the hydrochloride) thereof. The reaction may be carried out in the presence of an acid (e.g. p-toluenesulphonic acid) at an elevated temperature.

The invention is illustrated by the following Intermediates and Examples. All temperatures are in °C. Thin layer chromatography (t.l.c.) was carried out on silica. Solvent System A as used for t.l.c. denotes dichloromethane:ethanol: 0.88 ammonia solution and solvent System B denotes dichloromethane:methanol: 0.88 ammonia solution. $^1$H-N.m.r. spectra were obtained at 250 MHz for dilute solutions in d$_6$-dimethyl sulphoxide.

INTERMEDIATE 1

5,6-Dihydro-4-(2-methyl-2-phenylhydrazino)-2(1H)-pyridinone

1-Methyl-1-phenylhydrazine (21.6 g) was added to a suspension of 2,4-piperidinedione (20.0 g) in industrial methylated spirit (100 ml) at 20°–25° under nitrogen. The resultant solution was stirred for 3 h at room temperature. Water (300 ml) was added and the resulting suspension was filtered to give the title compound (34.4 g) as a solid, m.p. 180.5°–182°.

INTERMEDIATE 2

5,6-Dihydro-4-(2-phenylhydrazino)-2(1H)-pyridinone

Phenylhydrazine (17.4 ml) was added over 15 min to a stirred suspension of 2,4-piperidinedione (20 g) in ethanol (200 ml) at ca. 20°. The resulting suspension was diluted with ethanol (80 ml) and water (300 ml) and the solid was filtered off to give the title compound (23.31 g), m.p. 165°–168°.

INTERMEDIATE 3

3-Piperidinecarboxylic acid, 2,4-dioxo-, methyl ester, ion(1-), sodium

A mixture of N-(3-ethoxy-1,3-dioxopropyl)-β-alanine, methyl ester (10.8 g) and 21% w/w methanolic sodium methoxide (32 ml) in methanol (16 ml) was heated at reflux for ca. 3 h. The resulting suspension was cooled to ca. 0° and filtered to give the title compound (9.0 g) as a solid.

$^1$H-N.m.r. (D$_2$O): δ2.38(2H,t), 3.28(2H,t), 3.68(3H,s.).
IR (nujol mull): 3300, 1660, 1610 cm$^{-1}$.

INTERMEDIATE 4

5,6-Dihydro-4-(2-methyl-2-phenylhydrazino)-2(1H)-pyridinone

A suspension of 3-piperidinecarboxylic acid, 2,4-dioxo-, methyl ester, ion (1-), sodium (10.0 g) in water (24 ml) and 2M aqueous hydrochloric acid (26 ml) was heated at reflux for 30 min. The resulting mixture was cooled to ca. 20°, diluted with industrial methylated spirit (25 ml) and treated with 1-methyl-1-phenylhydrazine sulphate (2:1) (8.8 g) and 5M aqueous sodium hydroxide (12 ml). The resulting suspension was diluted with water (25 ml), cooled to ca. 0° and filtered to give the title compound (9.1 g), m.p. 185°.

INTERMEDIATE 5

5,6-Dihydro-4-(2-methyl-2-phenylhydrazino)-2(1H)-pyridinone

A mixture of 3-piperidinecarboxylic acid, 2,4-dioxo-, methyl ester (10.0 g) in industrial methylated spirits and water (1:1) (50 ml) and 5M aqueous hydrochloric acid (0.4 ml) was heated at 50°-55° for 30 min, and then heated at reflux for 1.5 h. The resulting mixture was cooled to room temperature and treated with 1-methyl-1-phenylhydrazine sulphate (2:1) (9.9 g) and 5M aqueous sodium hydroxide (11.6 ml). Water (5.5 ml) was added, and more water (33 ml) was added slowly over 45 min. The resultant solid was filtered off, washed with water (3×8 ml) and dried in vacuo at 43° to give the title compound (10.7 g), m.p. 180°-181°.

EXAMPLE 1

2,3,4,5-Tetrahydro-5-methyl-1H-pyrido[4,3-b]indol-1-one 5,6-Dihydro-4-(2-methyl-2-phenylhydrazino)-2(1H)-pyridinone (337 g) was added portionwise over 1.5 h to a stirred mixture of concentrated sulphuric acid (675 ml) and water (236 ml) at 13°-15°. The mixture was allowed to warm to ambient temperature over 2 h, then cooled to 13° and added dropwise to 2N sodium hydroxide (6.07l) at 10°. The resultant suspension was cooled to 8° and filtered. The solid product was triturated with water (2 l), then ethanol (0.85 l) at reflux, to provide the title compound (270 g), t.l.c. (System A, 100:8:1) Rf 0.41.

$^1$H-N.m.r.: δ3.04 (2H,t), 3.52 (2H,dt), 3.75 (3H,s), 7.08 (1H,br.t), 7.20 (2H,m), 7.53 (1H,dd), 7.96 (1H,dd).

EXAMPLE 2

2,3,4,5-Tetrahydro-5-methyl-1H-pyridol[4,3-b]indol-1-one

A solution of 5,6-dihydro-4-(2-methyl-2-phenylhydrazino)-2(1H)-pyridinone (100 g) in glacial acetic acid (200 ml) was added dropwise to concentrated sulphuric acid (200 ml) at 10°-20°. The mixture was stirred at ambient temperature for 1 h, then cooled to 10° and added slowly to 2N sodium hydroxide (1.8l) at 5°. The resultant suspension was cooled to 2° and filtered. The solid product was triturated with water (0.6l), then ethanol (250 ml) at reflux, to provide the title compound (72 g), m.p. 240°-245°, t.l.c. (System A, 100:8:1) Rf 0.41.

EXAMPLE 3

2,3,4,5-Tetrahydro-1H-pyrido[4,3-b]indol-1-one

A solution of 5,6-dihydro-4-(2-phenylhydrazino)-2(1H)-pyridinone (8.0 g) in acetic acid (16 ml) was added over 30 min to concentrated sulphuric acid (16 ml) at 10°-20°. The reaction mixture was stirred for 2 h, then added over 10 min to 2N sodium hydroxide (150 ml) at 15°-25°. The solid product was filtered off, triturated with water (50 ml), then recrystallised from ethanol (20 ml) and dried in vacuo to give the title compound (3.79 g), m.p. 255°, t.l.c. (System B, 100:8:1) Rf 0.2.

EXAMPLE 4

2,3,4,5-Tetrahydro-1H-pyrido[4,3-b]indol-1-one 5,6-Dihydro-4-(2-phenylhydrazino)-2(1H)-pyridinone (5.0 g) was added portionwise over 1 h to a mixture of concentrated sulphuric acid (10 ml) and water (3.5 ml) at ca. 20°, and the resulting mixture was aged for 18 h at ambient temperature. The solution was then added to a mixture of 2N sodium hydroxide (94 ml) and dichloromethane (20 ml). The solid product was filtered off and dried in vacuo at 45° to give the title compound (2.99 g), m.p. 255°, t.l.c. (System B, 100:8:1) Rf 0.2.

EXAMPLE 5

2,3,4,5-Tetrahydro-5-methyl-1H-pyrido[4,3-b]indol-1-one

Dimethylsulphate (2.28 ml) was added over 5 min to a stirred mixture of 2,3,4,5-tetrahydro-1H-pyrido[4,3-b]indol-1-one (3 g), acetone (12 ml) and 20% w/v aqueous sodium hydroxide (9 ml) at ca. 50°. The mixture was heated at reflux for 10 min. Further sodium hydroxide (6 ml) was added and the mixture was heated at reflux for 5 min. On cooling a solid crystallised. Water (10 ml) was added and the mixture was filtered. The solid was washed with water (2×20 ml), and dried in vacuo 45° to give the title compound (3.16 g). The t.l.c. data for this material were consistent with those obtained for the product of Example 1.

Analysis Found: C,71.8; H,6.2; N,14.0; C$_{12}$H$_{12}$N$_2$O requires C,72.0; H,6.0; N,14.0%.

EXAMPLE 6

2,3,4,5-Tetrahydro-5-methyl-1H-pyrido[4,3-b]indol-1-one

A solution of 5,6-dihydro-4-(2-methyl-2-phenylhydrazino)-2(1H)-pyridinone (250 g) in glacial acetic acid (500 ml) was added over ca. 2 h to concentrated sulphuric acid (500 ml) at 0°-5°. The mixture was stirred at 0°-5° for a further ca. 1 h then added over ca. 30 min. to 2N aqueous sodium hydroxide (4.5 l) at 20°-30°. The solid product was isolated by filtration, washed by displacement with water (4.5 l) and triturated with ethanol (625 ml) at reflux to provide the title compound (185 g), m.p. 240°-244°, t.l.c. (System A, 100:8:1) Rf 0.4

EXAMPLE 7

2,3,4,5-Tetrahydro-5-methyl-2-[(5-methyl-1H-imidazol-4-yl)methyl]-1H-pyrido[4,3-b]indol-1-one A mixture of 2,3,4,5-tetrahydro-5-methyl-1H-pyrido[4,3-b]indol-1-one (49.97 g), p-toluenesulphonic acid monohydrate (9.50 g) and 4-hydroxymethyl-5-methylimidazole hydrochloride (20.25 g) in N-methylpyrrolidinone (250 ml) was stirred and heated to 125°

(over 1 h) The reaction was then heated at 125°-130° for 4.5 h, during which time two further portions of 4-hydroxymethyl-5-methylimidazole hydrochloride (17.51 g and 6.88 g) were added. The reaction mixture was cooled, diluted with water (100 ml), and the stirred mixture was treated slowly with 8% aqueous sodium bicarbonate (750 ml). The resultant suspension was stirred in an ice bath for 1 h and then filtered to give a solid (57.64 g). A portion of this solid (11.09 g) was dissolved in dichloromethane (307 ml) and ethanol (166 ml), boiled with decolourising charcoal for 10 min and then filtered. The dichloromethane was distilled off at atmospheric pressure until the temperature of the mixture was at 65°. The stirred mixture was cooled and the resulting precipitate was filtered off to give the title compound (9.28 g), t.l.c. (System A, 50:8:1) Rf 0.55.

$^1$H-N.m.r: δ2.20(3H,s), 3.03(2H,t), 3.64(2H,m), 3.71(3H,s), 4.50(2H,s), 7.19(2H,m), 7.44(1H,s), 7.50(1H,d), 7.99(1H,d), 11.76(1H,s).

We claim:
1. A process for the preparation of a compound of formula (I):

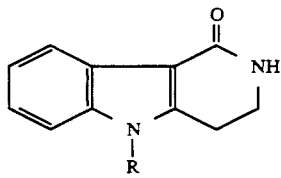

wherein R represents a hydrogen atom or a methyl or ethyl group, which comprises: cyclising a compound of formula (IV)

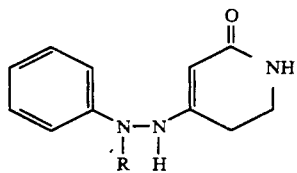

whereby said cyclisation is carried out either in the presence of 80 to 100% w/w sulphuric acid, a mixture of 100% w/w sulphuric acid and glacial acetic acid, 85% orthophosphoric acid or a hydrocarbylsulphonic acid; and
when R represents a hydrogen atom, optionally alkylating the compound of formula (I) to produce the compound of formula (I) in which R is methyl or ethyl.

2. A process according to claim 1 in which said cyclisation is carried out in the presence of sulphuric acid and a suitable co-solvent.

3. A process according to claim 1 in which said cyclisation is carried out in the presence of the hydrocarbylsulphonic, methanesulphonic acid.

4. A process according to claim 1, carried out in the presence of 80 to 100% w/w sulphuric acid or a mixture of 100% w/w sulphuric acid and glacial acetic acid at a temperature in the range 0° to 30° C.

5. A process according to claim 1, in which said compound of formula (IV) is prepared by reaction of 2,4-piperidinedione with a compound of formula PhNRNH$_2$ where R is a hydrogen atom or a methyl or ethyl group, or a salt thereof.

6. A process according to claim 5, in which said 2,4-piperidinedione is prepared from a compound of formula (V) or an alkali metal alkoxide thereof (Va)

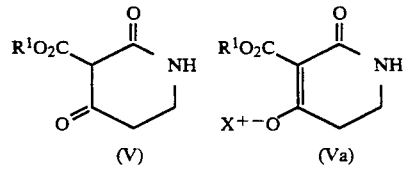

wherein R$^1$ represents a lower alkyl group and X represents an alkali metal, by hydrolysis and decarboxylation under acidic conditions at elevated temperature.

7. A process according to claim 6, in which said compound of formula (IV) is prepared directly by treating said compound of formula (V) or (Va) with a mineral acid at elevated temperature and subsequent reaction of the resultant cooled solution with a phenylhydrazine of formula PhNRNH$_2$ or a salt thereof without isolation of the 2,4-piperidinedione.

8. A process according to claim 6, in which said compound of formula (V) or (Va) is prepared from a compound of formula (VI)

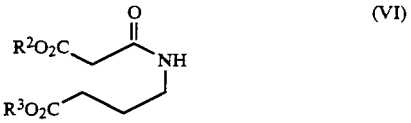

wherein R$^2$ and R$^3$ each independently represent lower alkyl groups, by reaction with an alkali metal alkoxide.

9. A process according to claim 1, for the preparation of a compound of formula (I) in which R represents a methyl group.

* * * * *